US012565669B2

(12) United States Patent
Alejandro Queipo et al.

(10) Patent No.: US 12,565,669 B2
(45) Date of Patent: Mar. 3, 2026

(54) OPTIMIZED PROCESS FOR PRODUCING SECOND-GENERATION SUGARS AND FERMENTATION PRODUCTS

(71) Applicant: Petróleo Brasileiro S.A.—Petrobras, Rio de Janeiro (BR)

(72) Inventors: Christian Alejandro Queipo, Rio de Janeiro (BR); Adriano Do Couto Fraga, Rio de Janeiro (BR); Luiz Fernando Martins Bandeira, Rio de Janeiro (BR)

(73) Assignee: Petróleo Brasileiro S.A.—Petrobras, Rio de Janeiro (BR)

( * ) Notice: Subject to any disclaimer, the term of this patent is extended or adjusted under 35 U.S.C. 154(b) by 644 days.

(21) Appl. No.: 17/797,216

(22) PCT Filed: Jan. 22, 2021

(86) PCT No.: PCT/BR2021/050035
§ 371 (c)(1),
(2) Date: Aug. 3, 2022

(87) PCT Pub. No.: WO2021/155452
PCT Pub. Date: Aug. 12, 2021

(65) Prior Publication Data
US 2023/0076406 A1　　Mar. 9, 2023

(30) Foreign Application Priority Data
Feb. 3, 2020　(BR) ..................... 10 2020 002320 9

(51) Int. Cl.
| | |
|---|---|
| *C12P 7/06* | (2006.01) |
| *C12P 7/10* | (2006.01) |
| *C12P 19/02* | (2006.01) |
| *C12P 19/04* | (2006.01) |
| *C12P 19/12* | (2006.01) |

(52) U.S. Cl.
CPC ................. *C12P 7/10* (2013.01); *C12P 19/02* (2013.01)

(58) Field of Classification Search
CPC ........ C13K 13/00; C13K 13/002; C13K 1/02; C12P 7/10; C13P 5/04; C13B 10/02; C10G 2300/1014
See application file for complete search history.

(56) References Cited

U.S. PATENT DOCUMENTS

| | | | |
|---|---|---|---|
| 9,976,195 B2 * | 5/2018 | Baudel ..................... C13B 5/04 |
| 2014/0053827 A1 | 2/2014 | Macedo Baudel et al. |

FOREIGN PATENT DOCUMENTS

| | | |
|---|---|---|
| BR | PI0802559 A2 | 3/2010 |
| BR | 112012031615-0 A2 | 11/2015 |
| BR | 112015015596-0 A2 | 7/2017 |
| WO | 2009102256 A2 | 8/2009 |
| WO | 2009155673 A1 | 12/2009 |
| WO | 2015120859 A1 | 8/2015 |
| WO | 2017029410 A1 | 2/2017 |
| WO | 2021155452 A1 | 8/2021 |

* cited by examiner

*Primary Examiner* — Maryam Monshipouri
(74) *Attorney, Agent, or Firm* — Morrison & Foerster LLP

(57) ABSTRACT

The present invention addresses to an optimized process for the production of ethanol from energy cane, by the integration of first-generation (1G) and second-generation (2G) technologies, which presents the advantages of reducing energy and water consumption. More specifically, the secondary juice from the second set of three rolls of mills of the conventional process (1G) is used for dilution, in the enzymatic hydrolysis step, in the cellulosic ethanol production process (2G).

10 Claims, 2 Drawing Sheets

OPTIMIZED PROCESS FOR PRODUCING SECOND-GENERATION SUGARS AND FERMENTATION PRODUCTS

CROSS-REFERENCE TO RELATED APPLICATIONS

This application is a national phase application, filed under 35 U.S.C. § 371, of PCT International Patent Application No. PCT/BR2021/050035, filed Jan. 22, 2021, and claims benefit of and priority to Brazilian application BR 10 2020 002320 9, filed on Feb. 3, 2020, the disclosures of all of which are incorporated herein by reference in their entirety.

FIELD OF THE INVENTION

The present invention addresses to an optimized process for the production of ethanol from energy cane, by the integration of first-generation (1G) with second-generation (2G) technologies, which has the advantages of reducing energy and water consumption. More specifically, the secondary juice from the second set of three rolls of mills of the conventional process (1G) is used for dilution, in the enzymatic hydrolysis step, in the cellulosic ethanol production process (2G). Such a fact reduces energy consumption because the secondary juice is directed to dilution in the enzymatic hydrolysis step of the second-generation process (2G), and no longer to the evaporators. At the same time, the use of secondary juice for dilution allows the reduction in the consumption of water and the concentration of sugars for the fermentation of the second-generation process (2G).

DESCRIPTION OF THE STATE OF THE ART

Currently, cellulosic ethanol is seen as an important alternative to assist in the decarbonization of the transport energy matrix. This is due to its characteristic of being produced from lignocellulosic wastes, which allows a low carbon footprint for this fuel.

In Brazil, one of the main raw materials for the production of cellulosic ethanol are the wastes of the sugar and alcohol industry, more specifically the bagasse and sugarcane straw. In this sense, a new variety of sugarcane, known as energy cane, has been developed. This variety of sugarcane has a higher fiber content than the traditional varieties, which makes it more attractive for the cellulosic ethanol (2G) production process.

Table 1 presents a comparative table between some of the characteristics of sugarcane and energy cane.

TABLE 1

Typical characteristics of sugarcane and energy cane. Source: KIM; DAY, 2010.

| Property | Sugarcane | Energy Cane |
|---|---|---|
| Harvest duration (months) | 10-12 | 10-15 |
| Number of cycles/year | 1 | 1 |
| Productivity (t/ha/year) | 70 | 100 |
| Brix (% juice) | 13-15 | 10-12 |
| Fiber (% sugarcane) | 13.5 | 26.7 |
| Fertilizer demand (N:P:K) | 300:150:150 | 300:150:150 |

The operation of an ethanol plant with energy cane follows the same macro process as a unit operating with traditional varieties of sugarcane. However, the operation of the juice extraction section has marked differences when operating with energy cane.

Thanks to the high fiber content, compared to traditional sugarcane, the juice extraction is comparatively more complicated, since the fibers tend to retain the sugars, which demands greater consumption of water to improve the recovery of these sugars.

The extraction of sugarcane juice is carried out by pressing the material by the mill rolls. In general, a group of 4 to 6 sets of three rolls of mill is employed in this operation. In the case of sugarcane juice extraction, 60% to 70% of the sugars are recovered during the first extraction (pressing in the first set of three rolls) and this juice is called primary juice.

The remaining sugars are extracted in the following sets of three rolls and normally with the injection of water in counter-current, this juice being called secondary juice. The mixture of primary juice and secondary juice make up the mixed juice, which is sent to the evaporators for concentration of sugars and then for fermentation.

The process of producing cellulosic ethanol (2G), from energy cane, consists of three main sequential steps: pre-treatment, enzymatic hydrolysis and fermentation. In the pre-treatment step, the main objective is to increase fiber exposure to enzymatic action in the subsequent step; for that, the most common strategies are steam explosion, by the action of water and heat, and acid hydrolysis. In the enzymatic hydrolysis, polymeric sugar fractions are converted to monomeric sugars, most notably glucose and xylose. Finally, in the fermentation step, these sugars are converted to ethanol.

During the energy cane processing steps, in the cellulosic ethanol unit, the operating conditions need to be adjusted to enable better throughputs. An example is the need to adjust the water:biomass ratio after the pre-treatment step. In general, the main pre-treatment technologies provide a pre-treated material with humidity of the order of 50-70%; however, for the enzymatic hydrolysis step, much higher water contents are required to allow the reaction medium to be stirred, reducing the diffusional restriction effect and providing more adequate performance of the added enzymes. At this step, the typical values of the water:biomass ratio are on the order of 5 to 10:1. That is, there is a need to add water to the medium.

Ideally, the addition of water in the enzymatic hydrolysis step should be as small as possible, as a more diluted hydrolysate generates lower concentrations of ethanol in the fermentation step, causing greater energy consumption in the distillation. However, if, on the one hand, a greater amount of water promotes the dilution of the sugars generated, on the other hand, a greater dilution reduces diffusional restrictions, allowing a more effective action of the enzymatic cocktail. In this way, the determination of the optimal water content in enzymatic hydrolysis is a function of the biomass and the enzyme cocktail used.

It should be noted that the processing of energy cane has some disadvantages. The first one involves the pressing phase, in first-generation (1G) units, in which the juice extraction is impacted by the material high fiber content, resulting in the need for greater water injection to obtain the secondary juice. In this aspect, the mixed juice obtained by mixing the primary and secondary juices is more diluted and this greater dilution of the juice leads to greater energy consumption in the evaporators.

In another aspect, the use of energy cane in second-generation (2G) units demands the addition of water to the medium, to adjust the water:biomass ratio in the enzymatic hydrolysis step, aiming at reducing the diffusional restriction effect and improve the performance of the added enzymes.

In order to improve the process of using energy cane, document BR1120150155960 proposes a process to produce fermentable sugars from whole biomass, in particular, fermentable sugars from sugarcane, whole energy cane and whole corn. For that purpose, in the pre-treatment phase, the biomass is introduced to a digester, in the presence of an acid catalyst and a solvent for the lignin. After the pre-treatment, the steps of hydrolysis and fermentation follow. It happens that, in this document, no form of integration between first and second-generation steps was proposed, which ends up not solving the technical problems related to the need of correcting the medium and reducing the energy consumption of the evaporators.

Further, regarding the attempts to solve the problems of energy cane processing, document BR112012031615 proposes the production of biofuels, wherein the raw material, including energy cane, is submitted to a crushing unit. In this process, there is an integration of the first and second-generation units, in which the fuel is generated. However, said document addresses to the integrated production of butanol and biodiesel and does not mention any relevant solution for the production of ethanol. More specifically, there is no integration between the hexoses extraction unit and the enzymatic conversion unit.

In order to improve the economic performance of plants operating with energy cane, the present invention proposes the integration of first-generation (1G) and second-generation (2G) ethanol production units. The integration between the first and second-generation units allows for the reduction of investment and operating costs by means of the sharing of equipment and reduction of energy consumption of the same, solving the indicated technical problems.

Thus, the process described in the present invention points to an efficient method of processing energy cane, which encompasses the use of secondary juice, generated in the extraction step of the first-generation (1G) unit, for dilution in the enzymatic hydrolysis step of the second-generation (2G) unit, replacing the addition of water. It is, therefore, a form of integration between the production units, which provides a visible improvement in the process, translated into the reduction of investments in equipment and operating costs.

BRIEF DESCRIPTION OF THE INVENTION

The present invention provides a better energy utilization by the integration of streams between the first and second-generation ethanol production units operating with energy cane. Thus, energy cane processing problems can be summarized in two intrinsic characteristics of the first and second-generation processes. These are:

a. The lower concentration of sugars in the secondary juice of energy cane extraction, in first-generation units, which causes an increase in energy consumption for evaporation and;

b. The need of adding water to adjust the consistency of the medium to allow enzymatic hydrolysis to occur under ideal conditions in the second-generation unit.

In order to solve the limitations described above, the present invention addresses to an optimized process for the production of ethanol from energy cane, by the integration of first-generation (1G) with second-generation (2G) technologies, which presents the advantages of reducing energy and water consumption. More specifically, the secondary juice from the second set of three rolls of mills of the conventional process (1G) is used for dilution, in the enzymatic hydrolysis step, in the cellulosic ethanol production process (2G). The present invention proposes an optimized process for the production of ethanol from energy cane, aiming at a processing with the integration of primary and secondary streams in order to reduce the energy expenditure of processing. For that purpose, after a first processing, the bagasse, with a residual sucrose content, is used for the formation of a secondary juice, used to adjust the consistency of the reaction medium and integration of said streams. Such a fact reduces energy consumption in the evaporators and eliminates the need to add water to adjust the consistency of the medium, which promotes enzymatic hydrolysis under ideal conditions in the second-generation unit.

BRIEF DESCRIPTION OF DRAWINGS

The invention can be better understood by means of the following detailed description, in consonance with the attached figures, where.

DETAILED DESCRIPTION OF THE INVENTION

Figure 1:
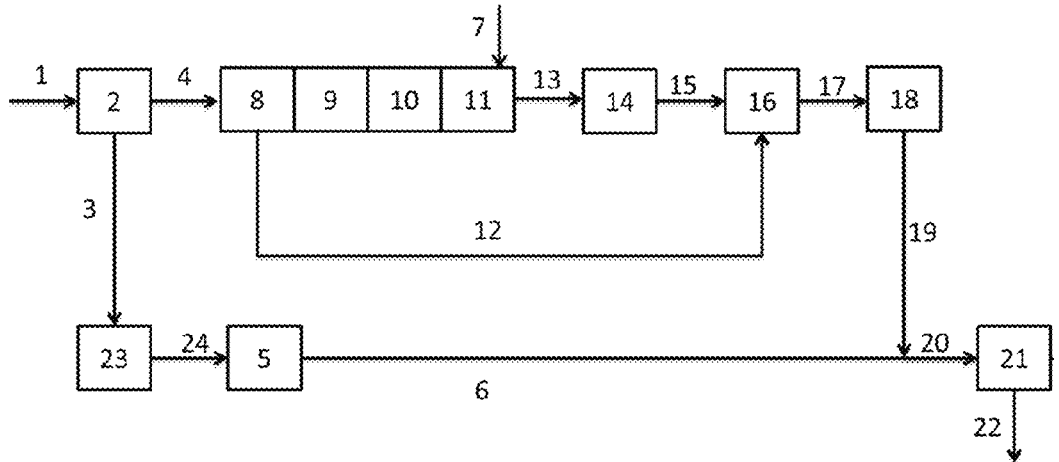
FIG. 1 schematically represents the process of the present invention.

FIG. 1 schematically shows the process proposed in the present invention. In this one, the first piece of equipment (2) is the first set of three rolls of the mill, which receives the energy cane (1) and, by pressing, generates the primary juice stream (3). The primary juice (3) is directed to the evaporators (23) to increase the sucrose concentration. The evaporated juice (24) then proceeds to the fermentation step of the first-generation process (5) where the sucrose contained in the juice is fermented to ethanol. The ethanol-containing stream from the first-generation (1G) fermentation is known as 1G wine (6). The bagasse, still with residual sucrose content (4), proceeds to the next sets of three rolls of mill (8 to 11). In these sets of three rolls of mill, water (7) is counter-currently injected and the secondary juice (12) is generated, with a low concentration of sugars (5 to 50 g/l).

The stream consisting of energy cane bagasse after the extractions (13) then proceeds to the pre-treatment step (14), already in the second-generation unit (2G) or cellulosic ethanol. In the pre-treatment step, the bagasse undergoes physicochemical changes and the product known as pre-treated (15) then proceeds to the enzymatic hydrolysis (16). This step uses the secondary juice (12) to adjust the consistency of the reaction medium (insoluble solids content of 5 to 25%). The stream (17) known as the hydrolysate is then sent to second-generation fermentation (18) where the sugars (mainly glucose and xylose) present in the hydrolysate are fermented to ethanol. The stream containing a high concentration of ethanol from this step is known as 2G wine (19). Ethanol-containing streams from the first-generation (6) and second-generation (19) sections are combined to form a single ethanol-containing stream (20) which is then sent to distillation (21) where ethanol is specified (22).

EXAMPLES

To confirm the feasibility of the presented hypothesis, a set of experiments was carried out to evaluate the impact of using an aqueous stream containing sugars, simulating the secondary juice of energy cane extraction, in the enzymatic hydrolysis step for the resuspension of the pre-treated biomass.

The pre-treated bagasse was washed to remove sugars, inhibitors and soluble acid lignin before carrying out the experiments. The tests were carried out with three different levels of insoluble solids (8% m/m; 12% m/m and 14% m/m), enzymatic load of 2.5% m/m (enzyme/dry sugarcane bagasse), 5 enzymatic hydrolysis times (8 h; 24 h; 48 h; 72 h and 96 h), with and without the addition of sugars and in duplicate.

The additions of sugars were carried out in the flasks for each condition and in order to have an initial concentration of 25 g of sucrose/L, 4 g of glucose/L and 4 g of fructose/L, simulating the use of the aqueous stream of extraction of the secondary juice. To evaluate the effects of this secondary juice stream, experiments without the addition of sugars were also carried out under the same conditions of insoluble solids content, enzymatic load and enzymatic hydrolysis times.

The hydrolysis efficiency was used as a response variable. This variable measures the recovery of sugars present in pre-treated sugarcane bagasse, after the enzymatic hydrolysis step.

Figure 2:
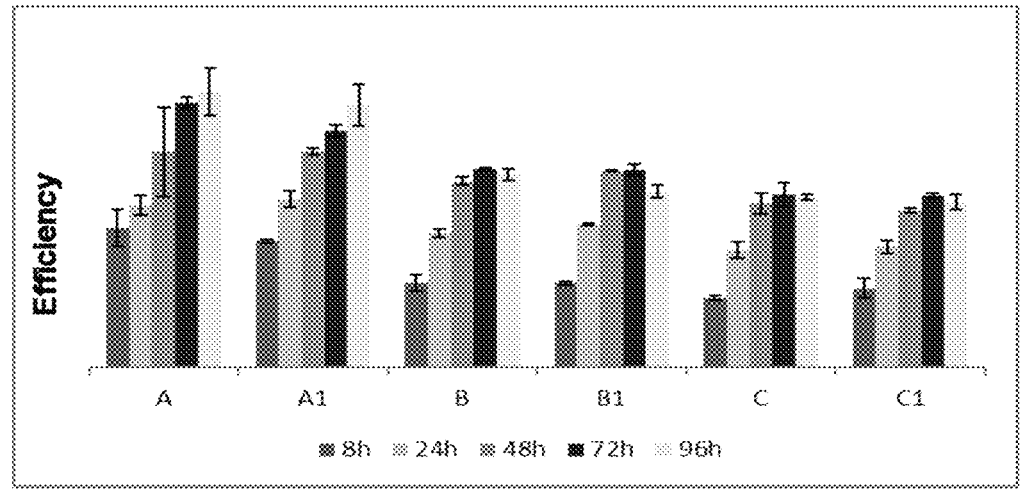
FIG. 2 presents the results of hydrolysis efficiency as a function of insoluble solids content (8%, 12% and 14%), with (A1, B1 and C1) and without the addition of sugars (A, B and C) (sucrose, glucose and fructose) at the hydrolysis times of 8 h, 24 h, 48 h, 72 h and 96 h.
Figure 3:
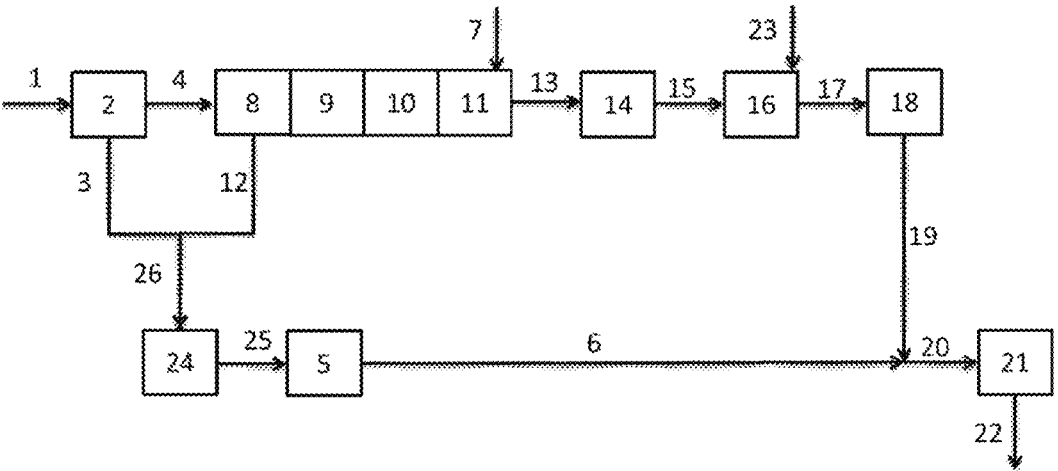
FIG. 3 schematically represents the traditional process.

FIG. 2 presents the results of hydrolysis efficiency as a function of insoluble solids content (8%, 12% and 14%), with (Tests A1, B1 and C1) and without the addition of sugars (Tests A, B and C) (sucrose, glucose and fructose) at the hydrolysis times of 8 h, 24 h, 48 h, 72 h and 96 h.

As expected, it is observed that the increase in solids content leads to a reduction in the hydrolysis efficiency. This phenomenon is often correlated with a worsening of mass transfer conditions and the loss of enzymes by unproductive adsorption, mainly in lignin.

Another observation that was also expected is related to the effect of increasing the enzymatic hydrolysis time. In general, longer hydrolysis times lead to efficiency gains, but the gains are greater in conditions of low solids content and in the region of shorter residence time (8 to 48 h). In fact, for solids contents greater than 8%, it was observed that the increase in residence times above 48 h did not bring significant advantages.

Regarding the inhibitory effect, considering the uncertainties of the experiments, the results obtained with and without the presence of sugars typically present in the secondary juice are equivalent, indicating that the solution is technically viable.

Accordingly, the present invention proposes an optimized process for the production of ethanol from energy cane, aiming at a processing with the integration of primary and secondary streams. This fact reduces energy consumption in the evaporators and eliminates the need of adding water to adjust the consistency of the reaction medium, which promotes enzymatic hydrolysis under ideal conditions in the second-generation unit.

The invention claimed is:

1. A process comprising the following steps:
   (a) processing energy cane by pressing, generating primary juice to be directed to evaporators;
   (b) concentrating the primary juice from step (a) in the evaporators;
   (c) fermenting the concentrated primary juice in a first-generation fermentation unit to form a first stream comprising ethanol;
   (d) processing a first bagasse from pressing of the energy cane with water injection in mill rolls generating secondary juice;
   (e) pre-treating a second bagasse from the secondary juice generation;
   (f) hydrolyzing the pre-treated second bagasse by enzymatic hydrolysis;
   (g) using the secondary juice to adjust a consistency of a reaction medium of the enzymatic hydrolysis; and
   (h) fermenting hydrolysate from the enzymatic hydrolysis to form a second stream comprising ethanol.

2. The process according to claim 1, wherein the first stream comprising ethanol from the first-generation fermentation unit and the second stream comprising ethanol are joined to form a single ethanol-containing stream.

3. The process according to claim 1, further comprising distilling the single ethanol-containing stream.

4. The process according to claim 1, wherein pressing the energy cane comprises pressing the energy cane in mill rolls.

5. The process according to claim 1, wherein the evaporators increase sucrose concentration of the primary juice.

6. The process according to claim 1 wherein the first-generation fermentation unit ferments sucrose in the concentrated primary juice to ethanol.

7. The process according to claim 1, wherein water is counter-currently injected in the mill rolls to generate the secondary juice, wherein the secondary juice has a low sugar concentration.

8. The process according to claim 1, wherein pre-treating the second bagasse from the secondary juice generation comprises physicochemical changing the second bagasse from the secondary juice generation.

9. The process according to claim 1, wherein the secondary juice is used to adjust the consistency of the reaction medium in the enzymatic hydrolysis allowing a reduction in energy expenditure of the process.

10. The process according to claim 1, wherein the hydrolysate is sent to a second-generation fermentation unit where sugars comprising glucose and xylose in the hydrolysate are fermented to ethanol.

* * * * *